United States Patent
Winterberg et al.

(10) Patent No.: US 8,633,345 B2
(45) Date of Patent: Jan. 21, 2014

(54) PROCESS FOR PREPARING ISOBUTENE BY CLEAVING MTBE-CONTAINING MIXTURES

(75) Inventors: Markus Winterberg, Datteln (DE); Dirk Roettger, Antwerp (BE); Rainer Bukohl, Marl (DE); Holger Wiederhold, Darmstadt (DE); Walter Luh, Marl (DE)

(73) Assignee: Evonik Oxeno GmbH, Marl (DE)

( * ) Notice: Subject to any disclaimer, the term of this patent is extended or adjusted under 35 U.S.C. 154(b) by 221 days.

(21) Appl. No.: 13/054,115

(22) PCT Filed: May 19, 2009

(86) PCT No.: PCT/EP2009/056069
§ 371 (c)(1),
(2), (4) Date: Jan. 14, 2011

(87) PCT Pub. No.: WO2010/006832
PCT Pub. Date: Jan. 21, 2010

(65) Prior Publication Data
US 2011/0118523 A1    May 19, 2011

(30) Foreign Application Priority Data
Jul. 17, 2008 (DE) .................... 10 2008 040 511

(51) Int. Cl.
*C07C 4/02* (2006.01)
(52) U.S. Cl.
USPC ............ 585/649; 585/638; 585/639; 585/648
(58) Field of Classification Search
USPC ................... 585/638, 639, 648, 649
See application file for complete search history.

(56) References Cited

U.S. PATENT DOCUMENTS

| | | |
|---|---|---|
| 6,657,090 B2 | 12/2003 | Rix et al. |
| 7,473,812 B2 | 1/2009 | Peters et al. |

(Continued)

FOREIGN PATENT DOCUMENTS

| | | |
|---|---|---|
| DE | 10 2006 040431 | 3/2008 |
| DE | 10 2006 040434 | 3/2008 |

OTHER PUBLICATIONS

Weissermel, K. et al. Industrial Organic Chemistry 3rd ed. Isoprene. 1997 pp. p. 119. http://books.google.com/books?id=AO5HyPl_X0wC&printsec=frontcover#v=onepage&q&f=false.*
Yasuyuki Matsumura, Keiji Hashimoto, Satohiro Yoshida, Dehydrogenation of methanol to formaldehyde over silicalite, Journal of Catalysis, vol. 100, Issue 2, Aug. 1986, abstract, ISSN 0021-9517, 10.1016/0021-9517(86)90106-5. (http://www.sciencedirect.com/science/article/pii/0021951786901065).*

(Continued)

*Primary Examiner* — Walter D Griffin
*Assistant Examiner* — Jelitza Perez
(74) *Attorney, Agent, or Firm* — Oblon, Spivak, McClelland, Maier & Neustadt, L.L.P.

(57) ABSTRACT

A process for preparing isobutene including cleaving a mixture obtained from an MTBE-containing feedstock and/or an MTBE-containing stream, affording a stream of reaction products consisting of isobutene, methanol, MTBE and by-products, the latter consisting of
 a1) high boilers having a boiling range above 55° C. at a pressure of 0.1 MPa;
 a2) medium boilers having a boiling range of 12 to 55° C. at a pressure of 0.1 MPa; and
 a3) low boilers having a boiling range below 12° C. at a pressure of 0.1 MPa;
distillatively separating into a stream which contains the isobutene product and low boilers, and a stream which contains MTBE, methanol, medium boilers and high boilers;
distillatively separating to obtain an MTBE-containing stream and a methanol-containing high boiler stream;
recycling an MTBE-containing stream in which the medium boilers being removed completely or partially before recycling.

20 Claims, 2 Drawing Sheets

(56) References Cited

U.S. PATENT DOCUMENTS

| | | |
|---|---|---|
| 7,737,318 B2 | 6/2010 | Santiago-Fernandez et al. |
| 7,932,428 B2 | 4/2011 | Rix et al. |
| 2007/0203369 A1 | 8/2007 | Praefke et al. |
| 2008/0058569 A1 | 3/2008 | Winterberg et al. |
| 2008/0058570 A1 | 3/2008 | Winterberg et al. |
| 2008/0058572 A1 | 3/2008 | Fernandez et al. |
| 2008/0058575 A1* | 3/2008 | Winterberg et al. .......... 585/703 |
| 2010/0081562 A1 | 4/2010 | Lansink Rotgerink |
| 2010/0144998 A1 | 6/2010 | Santiago-Fernandez et al. |

OTHER PUBLICATIONS

U.S. Appl. No. 13/381,680, filed Dec. 30, 2011, Winterberg, et al.
U.S. Appl. No. 13/381,676, filed Dec. 30, 2011, Boeing, et al.
U.S. Appl. No. 13/394,827, filed Mar. 8, 2012, Boeing, et al.
U.S. Appl. No. 13/880,862, filed Apr. 22, 2013, Winterberg, et al.
U.S. Appl. No. 13/808,010, filed Mar. 15, 2013, Boeing, et al.
International Search Report issued Feb. 9, 2010 in PCT/EP09/056069 filed May 19, 2009.

* cited by examiner

PROCESS FOR PREPARING ISOBUTENE BY CLEAVING MTBE-CONTAINING MIXTURES

The present invention relates to a process for preparing isobutene by cleaving MTBE-containing mixtures.

Isobutene is an important intermediate for the preparation of a multitude of organic compounds, for example for the preparation of butyl rubber, polyisobutylene, isobutene oligomers, branched $C_5$ aldehydes, $C_5$ carboxylic acids, $C_5$ alcohols and $C_5$ olefins. In addition, it is used as an alkylating agent, especially for synthesis of tert-butylaromatics, and as an intermediate for obtaining peroxides. In addition, isobutene can be used as a precursor for methacrylic acid and esters thereof.

Isobutene is present in customary industrial streams together with saturated and unsaturated $C_4$ hydrocarbons. Owing to the small boiling point difference and the low separation factor between isobutene and 1-butene, isobutene cannot be removed economically from these mixtures by distillation. Isobutene is therefore frequently obtained from industrial hydrocarbons by converting isobutene to a derivative which can be removed easily from the remaining hydrocarbon mixture, and by dissociating the isolated derivative to isobutene and derivatizing agent.

Typically, isobutene is removed from $C_4$ cuts, for example the $C_4$ fraction of a steamcracker, as follows: after removing the majority of the polyunsaturated hydrocarbons, principally the butadiene, by extraction and distillation or selective hydrogenation to linear butenes, the remaining mixture (raffinate I or selectively hydrogenated crack $C_4$) is reacted with alcohol or water. Isobutene forms methyl tert-butyl ether (MTBE) when methanol is used, and tert-butanol (TBA) when water is used. After they have been removed, these derivatives can be cleaved to isobutene in a reversal of their formation.

The cleavage of methyl tert-butyl ether (MTBE) to isobutene and methanol can be carried out in the presence of acidic or basic catalysts in the liquid phase or gas/liquid mixed phase or in the pure gas phase.

U.S. Pat. No. 5,567,860 describes a process for preparing high-purity isobutene. Here, isobutene-containing $C_4$ streams are first etherified with methanol, such that, according to the conversion, a mixture of MTBE, 2-methoxybutane (MSBE), unconverted $C_4$ hydrocarbons, methanol, water, dimethyl ether (DME), $C_4$ oligomers, and $C_3$ and $C_5$ hydrocarbons as an impurity of the $C_4$ stream, is obtained. This product mixture is separated by distillation into low boilers containing $C_3$, $C_4$ and $C_5$ hydrocarbons, methanol and DME, and high boilers containing $C_4$ oligomers. In a side draw of the column, MTBE and 2-methoxybutane (MSBE) are obtained, which are then fed to the acid-catalysed cleavage.

DE 10 2006 040431 describes a process for the preparation of isobutene by MTBE cleavage. In this process, starting MTBE together with a recycled MTBE stream are purified in a column by removing high boilers, and the resulting MTBE is cleaved. The reaction effluent is separated by distillation into isobutene with (azeotropic) proportions of methanol, and a mixture comprising the main constituents of methanol and unconverted MTBE. The methanol is subsequently removed for the most part from the methanol/MTBE mixture, and the MTBE-containing stream is recycled into the column for removal of high boilers. Optionally, low boilers are removed from the starting MTBE.

Published specification DE 10 2006 040430 is based on a comparable process. Characteristic features are purification of the MTBE used in the cleavage to less than 1000 ppm by mass of MSBE, and concentrations of linear butenes in the isobutene obtained below 1000 ppm by mass. The recycling of unconverted MTBE is optional.

Published specification DE 10 2006 040434 describes a process for cleaving MTBE, in which isobutene, with (azeotropic) proportions of methanol, is removed from the cleavage effluent in a first step. Subsequently, in a further distillation, methanol is obtained as the bottom product, as are a sidestream containing diisobutene, methanol and MTBE, and a top stream containing MTBE and methanol, the top stream being recycled into the cleavage. Accordingly, the high boilers formed in the process are discharged here via a sidestream.

The formation of high boilers by dimerization or oligomerization of the isobutene to $C_4$ oligomers, known as $C_8$ and $C_{12}$ components, is one of the known side reactions in MTBE cleavage. The undesired $C_8$ components are principally 2,4,4-trimethyl-1-pentene and 2,4,4-trimethyl-2-pentene.

In addition, particularly over basic catalysts, a portion of the methanol formed in the cleavage is converted to DME with elimination of water.

The further workup of the methanol-containing isobutene streams obtained in DE 10 2006 040431, DE 10 2006 040430 and DE 10 2006 040434 therefore envisages a removal of the methanol by extraction with water and a subsequent distillation, in which DME and water are removed from the isobutene.

MTBE cleavage in the gas phase has the advantage that it generally proceeds at higher temperatures. The equilibrium of the reaction of MTBE to give isobutene and methanol is thus more strongly on the side of the products, such that higher conversions can be achieved. Owing to the higher cleavage temperatures, however, other and/or additional side reactions can occur.

Figure 1:
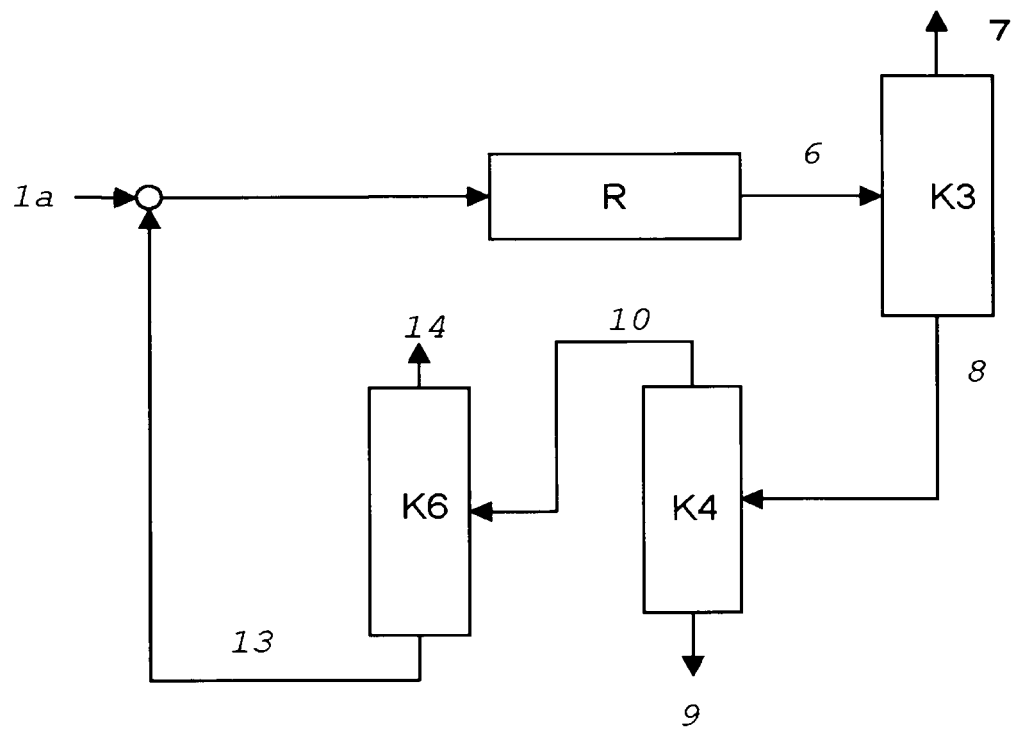
FIG. 1 shows a block diagram of a process in which MTBE is cleaved.

As described at the outset, isobutene is an important intermediate for the preparation of a multitude of organic compounds. The efficient preparation of these products is a core area of current industrial research and therefore places very high demands on the product purity.

It was therefore an object of the invention to develop a process in which high-purity isobutene, as required, for example, for the preparation of polyisobutene (PIB), butyl rubber or else of methyl methacrylate (MMA), becomes available. This object is achieved by a process for preparing isobutene from MTBE-containing mixtures, which comprises the following steps:

a) in a reactor R, cleaving a mixture obtained from an MTBE-containing feedstock (1a) and/or an MTBE-containing stream (13, 5), affording a stream (6) of reaction products consisting of isobutene, methanol, MTBE and by-products, the latter consisting of a1) high boilers having a boiling range above 55° C. at a pressure of 0.1 MPa;

a2) medium boilers having a boiling range of 12 to 55° C. at a pressure of 0.1 MPa; and a3) low boilers having a boiling range below 12° C. at a pressure of 0.1 MPa;

b) distillatively separating stream (6) into a stream (7) which contains the isobutene product and low boilers, and a stream (8) which contains MTBE, methanol, medium boilers and high boilers;

c) distillatively separating stream (8) to obtain an MTBE-containing stream (10, 12) and a methanol-containing high boiler stream (9, 11);

d) recycling an MTBE-containing stream (10, 12, 13) into step a) of the process, the medium boilers being removed completely or partially before step d) from the streams (10, 12) rich in medium boilers.

It has now been found that, surprisingly, the cleavage of MTBE in the gas phase forms reaction mixtures which have components whose normal boiling points are between those of the $C_4$ hydrocarbons and MTBE. Examples include dimethoxymethane and isoprene. Dimethoxymethane can form through dehydration of methanol to formaldehyde and the acetalization thereof with methanol. Isoprene can be formed from formaldehyde and isobutene. Since, based on the boiling sequence for $C_4$ hydrocarbons and MTBE, these are components of moderate boiling point, these components are referred to hereinafter as medium boilers. Their boiling point at 0.1 $MPa_{(abs)}$ is typically between 12° C. and 55° C.

The concentration of the medium boilers formed in the reaction is typically significantly below 500 ppm by mass based on the reactor effluent.

What is meant by these medium boilers is not $C_4$ hydrocarbons, for example 1-butene or cis- and trans-2-butene, which can form, for example, through cleavage of MSBE and boil only just above isobutene, and also isobutane, which can likewise be formed as a by-product of the cleavage.

TABLE 1

Boiling points of the $C_4$ hydrocarbons at 0.1 $MPa_{(abs)}$

| $C_4$ hydrocarbon | Boiling point [° C.] |
|---|---|
| isobutane | −11.74 |
| isobutene | −7.06 |
| 1-butene | −6.28 |
| 1,3-butadiene | −4.62 |
| n-butane | −0.53 |
| trans-2-butene | 0.87 |
| cis-2-butene | 3.56 |
| 1,2-butadiene | 10.85 |

If the medium boilers formed from the side reactions are not removed in the process, they can accumulate in the process and/or get into the isobutene product. For some applications of the isobutene, for example the preparation of polyisobutene (PIB) or butyl rubber, oxygenates or conjugates dienes, however, are troublesome.

Oxygenates such as dimethoxymethane have similar properties to the typically specified dimethyl ether (DME). Unlike DME, dimethoxymethane boils at higher temperatures than isobutene. This means that DME and dimethoxymethane cannot be removed from isobutene in one distillation step.

Isobutane formed from side reactions, in contrast, is generally uncritical at least in relatively small concentrations, since it is chemically substantially inert, and typical is isobutene specifications permit concentrations up to 1000 ppm in the product (see Table 5).

The relevant literature does not describe the formation of these medium boilers. Therefore, there is also no known process that envisages the removal of these medium boilers from the reaction mixture.

Nor do the processes described in U.S. Pat. No. 5,567,860, DE 10 2006 040431, DE 10 2006 040430 and DE 10 2006 040434 have any step for the removal of medium boilers. In these processes, these components, according to the operating method of the column arranged downstream of the reactor, would get either entirely or partly into the top product of this column and hence into the isobutene product.

In the case of removal via the bottom product, however, the recycling of the unconverted MTBE results in an enrichment of the medium boilers in the process. If the components pass through the reactor without any further reaction, the concentrations of the medium boilers would rise up to a limit in concentration at which they again get into the top product of the column arranged downstream of the reactor, thus ultimately getting into the isobutene fraction after all. Should there be any further reactions of the medium boilers in the reactor, there is the risk that additional components get into the isobutene or that the catalyst is damaged, for example as a result of coking.

Compared to the closest prior art, described in DE 10 2006 040431 and DE 10 2006 040430, the process according to the invention has the advantage that medium boilers formed in the process are discharged selectively.

In a preferred embodiment of the process, this is done together with the low and medium boilers of the starting MTBE, which keeps the additional technical demands and energy intensity low.

The means of removing the medium boilers additionally extends the operation of the cleavage to higher temperatures, since the formation of the medium boilers takes place to an increased degree at high temperatures. This can be utilized, for example, to prolong the catalyst lifetime or to reduce the amount of catalyst.

Cleavage Reaction

In step a) of the process according to the invention, MTBE is cleaved in the gas phase over a heterogeneous catalyst to give isobutene and methanol. In this step, it is possible to use all solid catalysts which bring about the cleavage of MTBE to isobutene and methanol within the temperature range of 150 to 500° C., especially within the range from 200 to 400° C.

The catalysts used in the process according to the invention may, for example, contain metal oxides, mixed metal oxides, especially those which contain silicon oxide and/or aluminium oxide, acids on metal oxide supports or metal salts or mixtures thereof.

In the process according to the invention, MTBE is cleaved to isobutene and methanol in the gas phase preferably using catalysts which consist in a formal sense of magnesium oxide, aluminium oxide and silicon oxide. Such catalysts are described, for example, in U.S. Pat. No. 5,171,920 in example 4 or in EP 0 589 557.

Particular preference is given to using catalysts which, in a formal sense, comprise magnesium oxide, aluminium oxide and silicon dioxide, and which have a proportion of magnesium oxide of 0.5 to 20% by mass, preferably of 5 to 15% by mass and more preferably of 10 to 15% by mass, a proportion of aluminium oxide of 4 to 30% by mass, preferably of 10 to 20% by mass, and a proportion of silicon dioxide of 60 to 95% by mass, preferably of 70 to 90% by mass. It may be advantageous when the catalyst comprises an alkali metal oxide in addition to the magnesium oxide. This may, for example, be selected from $Na_2O$ or $K_2O$. The catalyst preferably comprises $Na_2O$ as the alkali metal oxide. The catalyst used with preference preferably has a BET surface area (determined volumetrically with nitrogen to DIN ISO 9277) of 200 to 450 $m^2/g$, preferably of 200 to 350 $m^2/g$. When the catalyst is applied as an active material on a support, only the active material has a BET surface area within the range specified. The material composed of catalyst and support may, in contrast, according to the properties of the support, have a significantly different BET surface area, especially a lower BET surface area.

The pore volume of the catalyst is preferably 0.5 to 1.3 ml/g, preferably 0.65 to 1.1 ml/g.

The mean pore diameter to DIN 66133 of the catalyst is preferably 5 to 20 nm, preferentially 8 to 15 nm. More preferably, at least 50%, preferably more than 70%, of the total pore volume (sum of the pore volume of the pores with a pore diameter of greater than or equal to 3.5 nm, determined by mercury porosimetry to DIN 66133) of the catalyst, is accounted for by pores having a diameter of 3.5 to 50 nm (mesopores).

In the process according to the invention, preference is given to using catalysts which have a mean particle size (determined by screen analysis) of 10 μm to 10 mm, preferably 0.5 mm to 10 mm, more preferably a mean particle size of 1 to 5 mm. Preference is given to using solid catalysts which have a mean particle size $d_{50}$ of 2 to 4 mm, especially of 3 to 4 mm.

In the process according to the invention, the catalyst can be used in the form of shaped bodies. The shaped bodies may assume any shape. Preference is given to using the catalyst as shaped bodies in the form of spheres, extrudates or tablets. The shaped bodies preferably have the abovementioned mean particle sizes.

The preparation and use of such magnesium aluminosilicate catalysts is described in DE 10 2006 040432. Reference is made thereto.

The MTBE is cleaved in the gas phase within the temperature range from 150 to 500° C., especially 200 to 400° C., at pressures of 0.05 to 2 MPa, especially at pressures of 0.3 to 1 MPa, very particularly at pressures of 0.5 to 0.7 MPa.

The cleavage of MTBE to isobutene and methanol is an endothermic reaction. In order to prevent partial condensation of MTBE and products, it is appropriate to operate the reactor such that the minimum temperature in the reactor is greater than 150° C., preferably greater than 200° C. The input temperature of the MTBE, which can be established by means of a heater connected upstream of the reactor, is therefore at least 150° C., preferably at least 200° C.

In the course of operation, it may be advantageous to raise the input temperature up to 500° C. with increasing deactivation of the catalyst to keep the conversion constant. When the conversion can no longer be maintained on attaining of 500° C., it may be advantageous to completely or partially replace the catalyst.

The conversion of the MTBE in step a) of the process according to the invention is between 40% and 99%, preferably between 70% and 98%, more preferably between 85% and 95%.

The reactor is preferably operated with a weight hourly space velocity (WHSV, in kilograms of reactant per kilogram of catalyst per hour) of 0.1 to 5 h$^{-1}$, especially of 1 to 3 h$^{-1}$, in straight pass.

The reactors used are preferably tubular reactors or tube bundle reactors, especially those with internal tube diameters of 10 to 60 mm. They are preferably operated as described in DE 10 2006 040433.

In addition, it is possible to use plate reactors for the performance of the cleavage reaction. Plate reactors are of analogous construction to plate heat exchangers. The separation of the plates between which the catalyst is present is preferably 10-80 mm.

The temperature decline in the catalyst zone at any point in relation to the input temperature is preferably less than 50° C., more preferably less than 40° C. and most preferably 5 to 30° C. The maximum temperature decline can be adjusted by numerous parameters, for example by the temperature of the heat carrier used for heating, and by the speed with which the heat carrier flows through the jacket.

Side reactions occur in the cleavage of MTBE. These are attributable either to MTBE or the isobutene and methanol cleavage products.

A standard reaction which occurs in MTBE cleavage is the formation of dimethyl ether (DME). This is formed by reaction of two molecules of methanol to give DME and water. The process according to the invention is preferably operated such that the DME selectivity of the reaction for DME is less than 10%, preferably less than 4% (DME selectivity=2×[mol of DME formed]/[mol of MTBE converted]).

Reaction of isobutene with water can additionally result in formation of tert-butanol (TBA). The formation/cleavage of TBA is, however, an equilibrium reaction; when TBA is conducted into the reactor with the MTBE, it is normally partially cleaved.

A further side reaction is the formation of $C_8$ hydrocarbons by dimerization of isobutene. These consist principally of diisobutene, a mixture of 2,4,4-trimethylpentene-1 and 2,4,4-trimethylpentene-2.

In addition to the side reactions, there are usually also parallel reactions in which impurities from the MTBE react. These include, for example, the cleavage of 2-methoxybutane (MSBE) present in the MTBE. Through elimination of methanol, these can form 1-butene and 2-butenes. 3-Methoxy-1-butene or 1-methoxy-2-butene present in the MTBE can form 1,3-butadiene in the cleavage.

Raw Materials

The present invention is a process for preparing isobutene from MTBE. It is possible to use MTBE of different quality. In particular, it is possible to use technical-grade MTBE of various qualities or mixtures of technical-grade MTBE and methanol.

In order to obtain isobutene of high purity, it is advantageous to use a starting MTBE of high purity in step a) of the process. This can be obtained from technical-grade MTBE, which is generally intended for the fuel market, by purification. In preferred embodiments of the process according to the invention, this purification is part of the process, and so technical-grade MTBE can be used directly. Technical-grade MTBE (fuel quality) is therefore the preferred feedstock. Table 2 shows, for example, the typical composition of a technical-grade MTBE.

TABLE 2

Typical composition of technical-grade MTBE (fuel quality).

| Component | Proportion by mass [kg/kg] |
|---|---|
| 1-butene/2-butenes | 0.001000 |
| pentanes | 0.001500 |
| MTBE | 0.978000 |
| 2-methoxybutane (MSBE) | 0.003000 |
| methanol | 0.008500 |
| tert-butanol | 0.003000 |
| water | 0.000050 |
| 2,4,4-trimethylpentenes | 0.003300 |

Technical-grade MTBE can be prepared by known methods by reaction of $C_4$ hydrocarbon mixtures from which the polyunsaturated hydrocarbons have been substantially removed, for example raffinate I or selectively hydrogenated crack $C_4$, with methanol.

Purification of the Cleavage Products

The cleavage products from the reactor are separated by distillation in step b) of the process according to the invention. This affords a stream 7 which comprises more than 90% by mass of isobutene, low boilers and proportions of methanol, and a further stream 8 which contains methanol, MTBE, medium boilers and high boilers.

Table 3 shows the pure substance boiling points of components typically present in the reactor effluent at 0.5 $MPa_{(abs)}$. As well as isobutene, the low boilers present are further $C_4$ hydrocarbons (1-butene, 2-butenes) and DME. Isoprene and dimethoxymethane are medium boilers formed in the reaction with boiling points according to the table below. The high boilers present, i.e. components with a higher boiling point than MTBE, are TBA, diisobutene and MSBE.

TABLE 3

Pure material boiling points of components typically present in the reactor effluent at 0.5 $MPa_{(abs)}$

| Pure substance | Boiling temp. [° C.] | Typical proportion | |
|---|---|---|---|
| DME | 19.2 | 0.1-2% | by mass |
| isobutene | 42.7 | 50-60% | by mass |
| 1-butene | 43.4 | 0-150 | ppm by mass |
| trans-2-butene | 51.4 | 0-750 | ppm by mass |
| cis-2-butene | 54.1 | (sum of 2-butenes) | |
| isoprene | 90.4 | 10-300 | ppm by mass |
| dimethoxymethane | 95.9 | 5-150 | ppm by mass |
| methanol | 111.5 | 30-37% | by mass |
| MTBE | 113.8 | 3-25% | by mass |
| MSBE | 120.8 | 0-1700 | ppm by mass |
| TBA | 131.3 | 0-1000 | ppm by mass |
| diisobutene | 171.2 | 100-1000 | ppm |

Through appropriate design and operating mode of the distillative separation in step b) of the process according to the invention, it is possible to enrich the medium boilers for the most part or completely in stream 8, such that the isobutene-rich stream 7 is free or virtually free of these medium boilers.

The distillative separation of the cleavage products 6 is preferably effected in exactly one distillation column. This distillation column has preferably 20 to 55 theoretical plates, preferably 25 to 45 and more preferably 30 to 40 theoretical plates. The reflux ratio is, depending on the number of plates realized, the composition of the reactor effluent and the required purities of distillate and bottom product, preferably less than 5, preferentially less than 1. The operating pressure of the column can preferably be established between 0.1 and 2.0 $MPa_{(abs)}$. It is advantageous to operate the column at a lower pressure than the pressure with which the cleavage reactor (R) is operated. The reaction products 6 can then be transferred in gaseous form or partially in gaseous form, after partial condensation, to the distillation column. A compressor to raise the pressure or a complete condensation can thus be dispensed with.

More preferably, the reaction products 6 are transferred to the distillation column after partial condensation. Preference is given to condensing 30-70%, particular preference to condensing 40-70%, of the gas stream. The uncondensed gas stream is introduced directly into the column, and the condensed gas stream if necessary after increasing the pressure by means of a pump.

The gas phase and the liquid phase can be fed in at the same point or at different points in the column. Preference is given to feeding the liquid phase in at the same plate or one to five plates below the feed point of the gas phase.

The energy released in the partial condensation of the gas phase is preferably utilized elsewhere in the process, for example to heat a column or to preheat the reactor feed.

In order to be able to condense isobutene against cooling water at the top of the column, a pressure of approx. 0.5 $MPa_{(abs)}$ is needed. When the cleavage is conducted, for example, at a pressure of 0.65 $MPa_{(abs)}$, it may be advantageous when the distillation column is operated with an operating pressure of 0.55 to 0.6 $MPa_{(abs)}$. To heat the evaporator of the column, for example, 0.4 MPa steam can be used. The bottom product obtained is stream 8, the top product stream 7. The latter contains more than 90% by mass, preferably more than 95% by mass, of isobutene based on the overall top product.

Optionally, the column can be designed as a reactive distillation. This has the advantage that the MTBE conversion in the overall process can be increased by cleaving a portion of the MTBE unconverted in the cleavage reactor to isobutene and methanol in the reaction part of the reactive distillation column. The design of the column as a reactive distillation is described, inter alia, in the published specification DE 102006040430.

The content of linear butenes in the stream 7 is, based on the $C_4$ olefin fraction, preferably less than 10 000 ppm by mass, preferentially less than 5000 ppm by mass and more preferably less than 1000 ppm by mass. The content of 1-butene in stream 7, based on the $C_4$ olefin fraction, is preferably less than 5000 ppm by mass, preferentially less than 1000 ppm by mass and more preferably less than 500 ppm by mass. The content of 2-butenes (sum of the two 2-butenes) is, based on the $C_4$ olefin fraction, preferably likewise less than 5000 ppm by mass, preferably less than 2000 ppm by mass and more preferably less than 500 ppm by mass.

A noninventive removal of the medium boilers together with the isobutene and the low boilers is technically likewise possible. It is then possible to remove the medium boilers from the isobutene, if appropriate after removing methanol. In this case, they are, however, obtained as the bottom stream, whereas the entire amount of isobutene is obtained as the top product. This is less advantageous in technical terms.

The majority of the methanol present is removed in step c) from the stream 8 obtained in step b) of the process. Table 4 below shows the boiling points of the pure MTBE, MSBE, methanol, TBA and diisobutene substances, and also, by way of example of medium boilers formed in the reaction, the boiling points of isoprene and dimethoxymethane at 0.1 $MPa_{(abs)}$. For the diisobutene which occurs in two isomers, the boiling point of 2,4,4-trimethylpent-1-ene was listed by way of example. It is evident that the boiling point rises in the sequence of isoprene, dimethoxymethane, MTBE, MSBE, methanol, TBA and diisobutene. At the same time, however, the isoprene, MTBE, MSBE and diisobutene components form minimum azeotropes with methanol. The boiling points of these azeotropes and the composition is likewise listed in table 4, the azeotropes having been calculated with the "UNIFAC-DMD" property method (see J. Gmehling, J. Li, and M. Schiller, Ind. Eng. Chem. Res. 32, (1993), pp. 178-193) with the steady-state simulation program ASPEN Plus (version 12.1 from AspenTech). Under this boundary condition, the isoprene-methanol azeotrope is the low boiler in the system and can be obtained as the top product when the separation is carried out in a single column. When, however, the intention is to generate virtually pure methanol as the bottom product, the pure isoprene and dimethoxymethane materials and the MTBE-methanol, MSBE-methanol and diisobutene-methanol azeotropes additionally have to be distilled via the top. As the sole secondary component—in addition to water, which is not listed in the table, and the methanol product of value—TBA remains in the bottom product.

TABLE 4

Boiling points of the pure materials and the azeotropes with methanol at 0.1 MPa$_{(abs)}$; the azeotropes werecalculated with the "UNIFAC-DMD" property method.

| Pure substance/Azeotrope | Boiling temp. [° C.] | Composition [% by mass] | |
|---|---|---|---|
| Isoprene + methanol azeotrope | 30.5 | isoprene/methanol | 91.69/8.31 |
| Pure isoprene | 33.7 | | |
| Pure dimethoxymethane | 41.6 | | |
| MTBE + methanol azeotrope | 50.5 | MTBE/methanol: | 86.22/13.78 |
| MSBE + methanol azeotrope | 54.1 | 2-methoxybutane/methanol: | 80.40/19.60 |
| Pure MTBE | 54.7 | — | |
| Methanol + diisobutene azeotrope | 59.2 | methanol/diisobutene | 47.84/52.16 |
| Pure MSBE | 60.8 | — | |
| Pure methanol | 64.2 | — | |
| Pure TBA | 82.1 | — | |
| Pure 2,4,4-trimethylpentene-1 | 101.1 | — | |

The distillative removal of the methanol from the bottom product 8 is effected in one or more distillation column(s), preferably in one distillation column.

When a distillation column is used, it preferably has 20 to 75 theoretical plates, preferentially 30 to 65 and more preferably 35 to 50. It may be advantageous when the column, depending on the number of plates realized and the MTBE conversion achieved in the cleavage reactor, is operated with a reflux ratio of less than 10, preferably of 0.5 to 5. The operating pressure of the column is preferably adjusted to a value in the range from 0.05 to 1 MPa$_{(abs)}$, preferably from 0.1 to 0.3 MPa$_{(abs)}$. To heat the column, for example, 0.4 MPa steam can be used. The condensation can, according to the operating pressure selected, be effected against cooling brine, cooling water or air.

The methanol removed in step c) of the process contains preferably greater than 97% and more preferably greater than 99% by mass of methanol. The TBA content in the bottom product is preferably between 500 and 2000 ppm by mass and the water content preferably 0.5 to 0.8% by mass. The medium boilers formed in the reaction part, for example isoprene and dimethoxymethane, are preferably present at less than 200 ppm, preferably less than 100 ppm and more preferably less than 50 ppm. The methanol thus has a sufficiently high purity that it can be used for customary industrial syntheses, for example esterifications or etherifications. If required, the methanol can, though, also be concentrated to even higher purities in a further distillation step.

The stream 10 obtained in step c) of the process after the removal of methanol contains, as well as the main MTBE constituent, also methanol and the medium boilers formed in the reaction part, for example isoprene and/or dimethoxymethane. According to the invention, the medium boilers are removed from stream 10 before it is recycled into step a) of the process.

The medium boilers can be removed by distillation from stream 10 in one column or in a plurality of columns. It may additionally be advantageous to combine the removal of the medium boilers from stream 10 with the purification of the starting MTBE.

The present invention is illustrated in detail with reference to FIGS. 1 to 4, without any intention that the invention be restricted to the embodiments depicted there by way of example.

A block diagram of a preferred embodiment with which the process according to the invention can be performed is shown in FIG. 1. The starting MTBE 1a is conducted together with the return stream 13 into the cleavage reactor (R). The cleavage product 6 is separated in the column (K3) into a top product 7 which contains the isobutene formed, DME and, owing to azeotrope formation between isobutene and methanol, proportions of methanol, and into a bottom product 8 comprising the unconverted MTBE and the majority of the methanol formed. The bottom product 8 also contains the medium boilers formed in the reaction part, for example isoprene and/or dimethoxymethane.

The majority of the methanol and water is removed as the bottom product 9 from stream 8 in column (K4). In column (K6), the medium boilers 14 are removed from stream 10 and the principally MTBE-containing return stream 13 is recycled into the cleavage.

Figure 2:
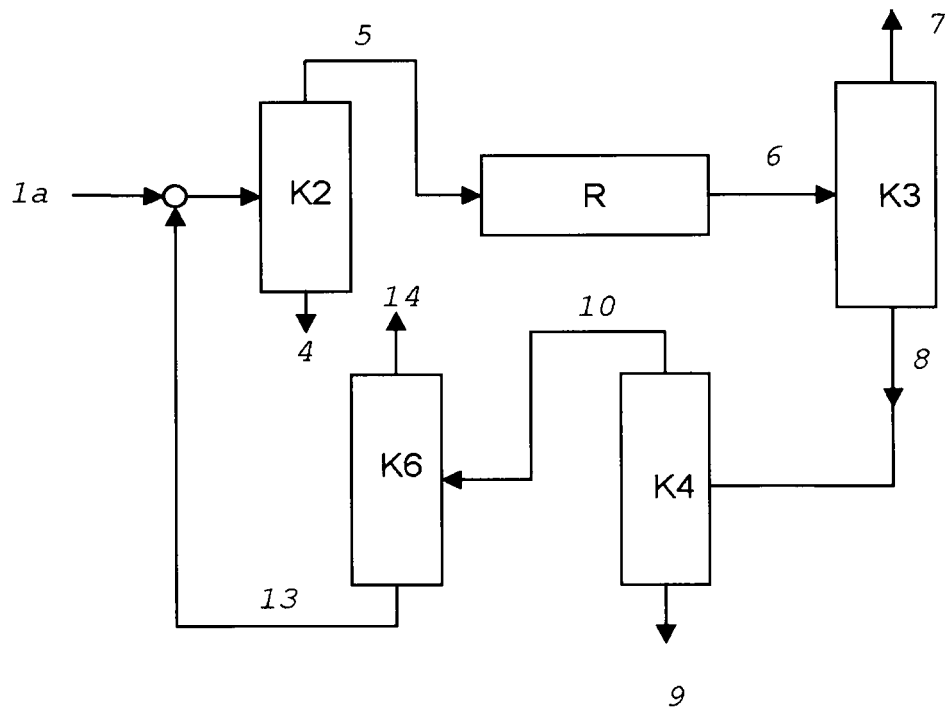
FIG. 2 shows a block diagram of a process in which high boilers are removed from a MTBE stream.

A further preferred embodiment of the process is shown in FIG. 2. In this embodiment, high boilers 4 are additionally removed at least partially from the starting MTBE 1a and the MTBE-containing return stream 13 in column (K2) before they are fed into the cleavage reactor (R). The distillate obtained is stream which is conducted into the cleavage reactor (R). The further workup is effected as described below under FIG. 1.

Figure 3:
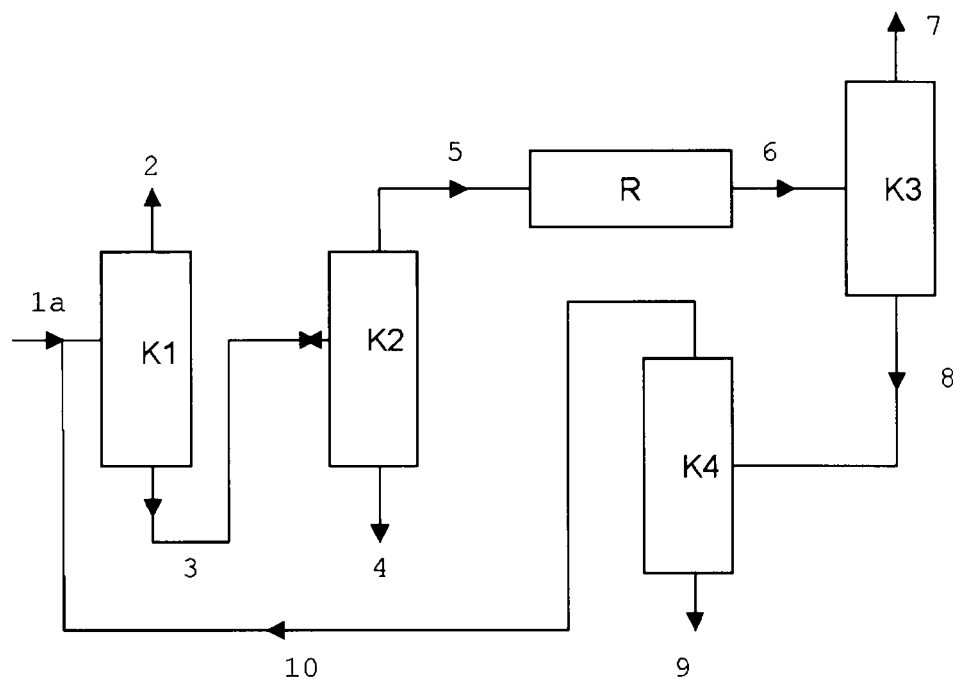
FIG. 3 shows a block diagram of a process in which MTBE is fractionated.

FIG. 3 shows a further preferred embodiment of the process. The starting MTBE 1a is fractionated together with stream 10 in column (K1). The return stream 10 contains, as well as the unconverted MTBE and methanol, also the medium boilers formed in the reaction part (R), for example isoprene and/or dimethoxymethane. In column (K1), these medium boilers are removed partially as top product 2 together with any low and/or medium boilers present in the starting MTBE 1a. The bottom product 3 is passed into column (K2). There, high boilers (diisobutene, MSBE) present are removed at least partially as bottom product 4. The top product 5 is passed into the cleavage reactor (R). The cleavage product 6 is separated in column (K3) into a top product 7 which contains the isobutene formed, DME and, owing to azeotrope formation between isobutene and methanol, proportions of methanol, and into a bottom product 8 comprising the unconverted MTBE and the majority of the methanol formed. The bottom product 8 also contains the medium boilers formed in the reaction part, for example isoprene and/or dimethoxymethane.

The majority of the methanol and water is removed as bottom product 9 from stream 8 in column (K4). The top product 10, which contains MTBE, a proportion of the methanol and the medium boilers formed in the reaction part, for example isoprene and/or dimethoxymethane, is purified together with the starting MTBE 1a in column (K1).

Optionally, columns (K1) and (K2) can be replaced by a single dividing wall column.

The configuration of the process according to FIG. 3 offers the advantage that technical-grade MTBE can be used directly in the process. Low boilers present are removed in column (K1) together with the medium boilers formed in the process. This combination gives rise to the potential advantage of saving one column. The is high boilers from the process and from the starting MTBE (for example MSBE) are removed together in column (K2).

Figure 4:
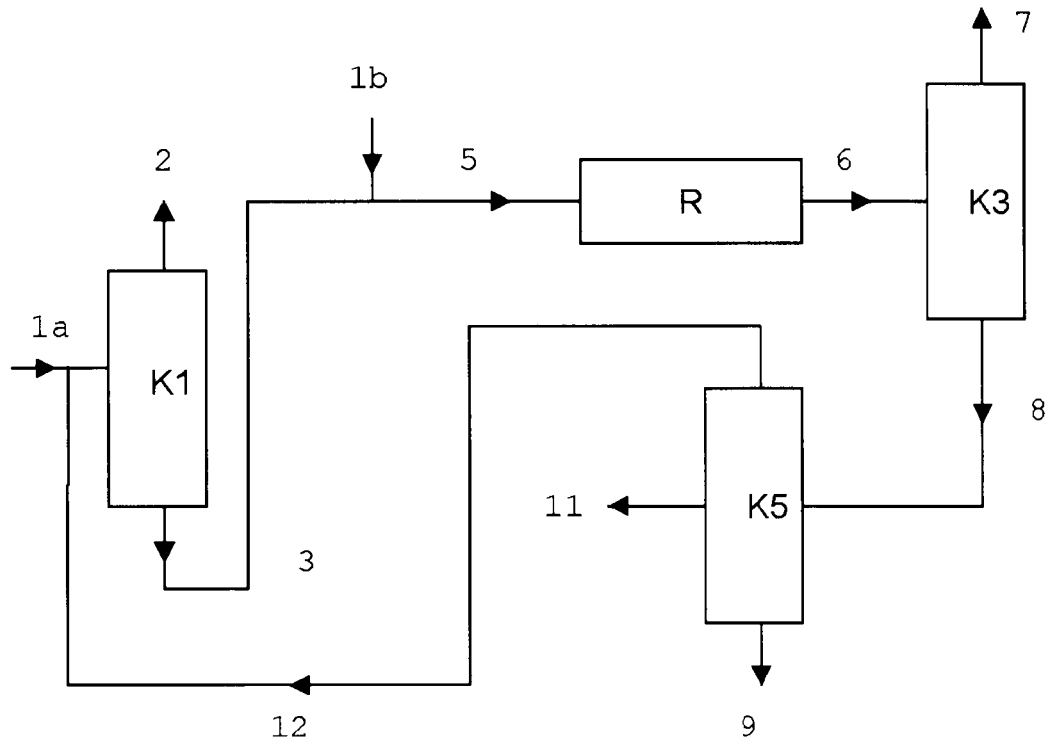
FIG. 4 shows a block diagram of a process in which medium boilers are partially removed from a top product.

A block diagram of a further preferred embodiment of a plant in which the process according to the invention can be carried out is shown in FIG. 4. The starting MTBE 1a is fractionated together with the MTBE-retaining return stream 12 in column (K1). This return stream 12 contains, as well as the unconverted MTBE and methanol, also the medium boilers formed in the reaction part (R), for example isoprene and/or dimethoxymethane. In column (K1), these medium boilers are removed partially as top product 2 together with the low boilers which may be present in the starting MTBE ($C_4$ and $C_5$ hydrocarbons). The bottom product is passed into the cleavage reactor (R). The cleavage product 6 is separated in column (K3) into a top product 7 which contains the isobutene formed, DME and, owing to azeotrope formation between isobutene and methanol, proportions of methanol, and into a bottom product 8 comprising the unconverted MTBE and the majority of the methanol formed. The bottom product 8 also contains the medium boilers formed in the reaction part, for example isoprene and/or dimethoxymethane.

Column (K5) constitutes a possible configuration of step c) of the process according to the invention. Therein, stream 8 is separated into a bottom product 9, into a sidestream 11 and into a top product 12. The bottom product 9 contains preferably more than 98% methanol. With the sidestream 11, diisobutene and any further high boilers, for example MSBE, are discharged. The MTBE, a proportion of the methanol and the medium boilers formed in the cleavage reactor, for example isoprene and/or dimethoxymethane, are obtained as the top product 12 and fed together with the starting MTBE 1a into the column (K1).

The embodiment according to FIG. 4 is of interest in particular for those MTBE starting mixtures which contain small amounts of diisobutene and MSBE. In this case, it is possible to dispense with column K2 for removing these components upstream of the reaction part, which simplifies the process. When the starting MTBE does not contain any low boilers, it can be passed directly into the cleavage reactor as stream 1b. In column K1, only the medium boilers are then removed as stream 2.

According to the invention, what is common to all embodiments is that there is a column in which medium boilers formed in the cleavage reactor (R) are removed via the top.

The distillative removal of the medium boilers formed in the cleavage reactor (R), for example isoprene and/or dimethoxymethane, instead of being effected in columns (K6) or (K1), can also be effected from another stream, for example from stream 8 (FIG. 1) or stream 5 (FIG. 2). These options too are embodiments of the process according to the invention, even if they are not considered separately.

Material Separation

Embodiments and operating parameters preferred for columns K1, K2, K5 and K6 designated in FIGS. 1 to 4 are specified hereinafter.

Column (K1), FIGS. 3 & 4

In column (K1), according to the invention, medium boilers formed in the reaction part, for example dimethoxymethane and/or isoprene, are removed from the return stream (10 or 12) consisting predominantly of MTBE. In addition, low boilers ($C_4$ and $C_5$ hydrocarbons) can be removed from the technical-grade MTBE.

Preference is given to performing the material separation in a distillation column which has 30 to 85 theoretical plates, preferably 40 to 75 and more preferably 40 to 60 theoretical plates. Preference is given to operating the column, depending on the number of plates realized, the composition of the MTBE used and the required purity of $C_4$ and $C_5$ hydrocarbons and of the medium boilers formed in the reaction part, for example dimethoxymethane and/or isoprene, with a reflux ratio between 50 and 350, especially between 120 and 300. The column is preferably operated with an operating pressure of 0.2 to 0.6 $MPa_{(abs)}$, preferably of 0.3 to 0.4 $MPa_{(abs)}$. To heat the column, for example, steam can be used. The condensation can, according to the operating pressure selected, be effected against cooling brine, cooling water or air. The top vapours of the column can be condensed completely or only partially, such that the top product 2 can be drawn off either in liquid or vaporous form. The top product 2 can be utilized thermally or be used as a feedstock of a synthesis gas plant.

Column (K2), FIGS. 2 & 3

In column (K2), the stream comprising MTBE is distilled to remove high boilers, especially diisobutene and/or MSBE, from the MTBE. When primarily only diisobutene is to be removed in the column, it may be advantageous when the column has 15 to 60 theoretical plates, preferably 20 to 55 and preferentially 30 to 45 theoretical plates. The reflux ratio, defined in the context of the present invention as the mass flow of the reflux divided by the mass flow of the distillate, is set, as a function of the number of stages realized, the composition of the MTBE used and the required purity, preferably to a value of 0.5 to 7, preferentially of 1 to 4.

When diisobutene and additionally MSBE are to be removed in the column, the distillation column used has preferably 50 to 140 theoretical plates, preferably 60 to 120 and most preferably 80 to 110. Depending on the number of plates realized, the composition of the MTBE used and the required purity, the reflux ratio is preferably 1 to 20, preferentially 3 to 10.

To increase the flexibility with regard to the quality of the starting MTBE 1a and to the required purity of the isobutene prepared, it may particularly be advantageous to provide a column with which both substances can be removed, i.e. a column which has preferably 50 to 140 theoretical plates. Even if the removal of MSBE should be unnecessary, the larger column need not be a disadvantage, since a portion of the higher capital investment for the larger column can be compensated for by energy savings (reduction in the reflux ratio).

The operating pressure can, irrespective of whether only diisobutene or additionally MSBE is to be removed, preferably be 0.1 to 2.0 $MPa_{(abs)}$. When the cleavage of the top product 5 in the cleavage reactor is effected in the gas phase at elevated pressure, it may be advantageous to perform the distillation at higher pressure, in which case the top condenser is preferably operated as a partial condenser and the top product 5 is drawn off in vaporous form. When the reaction pressure in the cleavage reactor is, for example, 0.7 $MPa_{(abs)}$, the distillation pressure should preferably be at least 0.75 $MPa_{(abs)}$. At operating pressures of greater than 1.3 $MPa_{(abs)}$, low-pressure steam can be obtained with the heat of condensation, and can be used to heat other columns in the process. To heat the column, according to the operating pressure selected, steam or heat carrier oil can be used. The bottom product 4 may contain, in addition to the high boilers, for example MSBE and diisobutene, also MTBE. This mixture can be utilized thermally, can be used as a feedstock for a synthesis gas plant, or be used directly or after hydrogenation as a fuel component.

The composition of the feed to the column (K2) may vary depending on the starting MTBE 1a and the degree of conversion of the MTBE in the cleavage reactor (R) (straight pass). In the case of use of MTBE of the composition according to table 2 and an MTBE conversion which is in the range from 50 to 95%, the feed to the column has in the range from 85 to 97% by mass of MTBE; the methanol content is in the range from 2 to 12% by mass. The diisobutene content is in the range from 1500 to 5000 ppm by mass; the MSBE content is in the range from 3500 to 5000 ppm by mass. Medium boilers formed in the reaction part, for example dimethoxymethane and/or isoprene, are preferably present at less than 200 ppm, preferentially less than 100 ppm and more preferably less than 50 ppm. Further components present include TBA, water and possibly linear butenes.

The bottom product 4 in column (K2) typically contains the high boilers diisobutene and MSBE, and also MTBE. If principally diisobutene is to be removed in the column, the MTBE content in the bottom product can be reduced to values less than 25% by mass. If MSBE is additionally to be removed, owing to the small boiling point differences between MSBE and MTBE, a higher MTBE content is preferably permitted in the bottom product, preferably in the range from 60 to 85% by mass, in order to reduce the complexity for the separation.

The removal of high boilers such as diisobutene via the bottom of the column (K2) has the advantage that only a small amount of, if any, high boilers get into the cleavage reactor. This can possibly protect the catalyst from accelerated deactivation, which can arise in the case of coverage with high boilers and possibly coking.

Column (K5), FIG. 4

The distillative separation is effected preferably under such conditions that very substantially pure methanol is obtained as the bottom product 9, that the predominant portion of the MTBE and all medium boilers formed in the reaction, for example isoprene and/or dimethoxymethane, are obtained in the top product 12, and that preferably more than 50% of the diisobutene present in the feed 8, preferentially more than 80%, more preferably more than 95%, is obtained in the sidestream 11. The side product simultaneously also constitutes an outlet for any MSBE which is present in the reactant and has not been converted in the cleavage, such that excessive concentration of this component in the circuit is prevented. Limiting the concentration of MSBE in the circuit simultaneously prevents an impermissibly high value of linear butenes formed by cleavage of MSBE in the reaction part in the isobutene product. The top product 12 is preferably recycled into column (K1) (FIG. 4).

As can be seen from table 4, the isoprene-methanol azeotrope is the low boiler in the system and can be obtained as the top product in the column used. At the same time, it is also possible for isoprene, dimethoxymethane and the MTBE-methanol and MSBE-methanol azeotropes to be distilled via the top. Diisobutene forms an azeotrope with methanol, which boils between the MTBE-methanol azeotrope and pure methanol. The diisobutene-methanol azeotrope can thus be removed in a sidestream, such that virtually diisobutene-free top and bottom products can be generated in one column. The bottom product obtained is thus virtually pure methanol which contains, as the sole secondary component—in addition to water, which is not listed in table 4-tert-butanol.

The distillation column (K5) used has preferably 20 to 80 theoretical plates, preferably 30 to 70 and more preferably 40 to 60 theoretical plates. The sidestream can be withdrawn below or above the addition point of the column feed. Preference is given to withdrawing the sidestream above, more preferably between 2 and 12 theoretical plates above, the feed point of the column feed. The column, depending on the number of stages realized and on the MTBE conversion achieved, is preferably operated with a reflux ratio of less than 10, preferentially of 0.5 to 5. The operating pressure of column (K5) is preferably adjusted to a value in the range from 0.05 to 1 MPa$_{(abs)}$, preferably from 0.1 to 0.3 MPa$_{(abs)}$. To heat the column, for example, 0.4 MPa of steam can be used. According to the operating pressure selected, the condensation can be effected against cooling brine, cooling water or air.

The resulting bottom product 9 contains preferably more than 98% by mass of methanol, preferably more than 99% by mass. The TBA content in the bottom product is preferably 500 to 3000 ppm by mass; the water content is preferably 0.5 to 0.8% by mass. The medium boilers formed in the reaction part, for example isoprene and dimethoxymethane, are preferably present at less than 200 ppm, preferably less than 100 ppm and more preferably at less than 50 ppm. The methanol thus has a sufficiently high purity that it can be used for customary industrial syntheses, for example esterifications or etherifications. If required, the methanol can, however, also be concentrated to even higher purities in a further distillation step.

The resulting top product 12 preferably contains the predominant portion of the MTBE and methanol present in the feed stream 8, the medium boilers formed in the reaction part, for example dimethoxymethane and isoprene, and possibly MSBE, and is preferably recycled into column (K1). The MTBE content is, according to the distillation conditions and column pressure, preferably in the range from 65 to 88% by mass, preferentially in the range from 75 to 85% by mass. The methanol content is preferably in the range from 10 to 35%, preferentially in the range from 12 to 18%. The MSBE content is preferably in the range from 0.5 to 5% by mass. When the feed stream 8 contains isoprene, the isoprene content is preferably less than 1% by mass. When the feed stream 8 contains dimethoxymethane, the dimethoxymethane content is preferably less than 5000 ppm by mass.

The resulting sidestream 11 preferably contains virtually the entire amount of the diisobutene present in the feed stream 8. In addition, the sidestream, according to the mode of operation of the column, may contain in the range from 10 to 40% by mass of the MSBE present in the feed stream 8. Since, according to the mode of operation and catalyst used, the MSBE is not converted fully in the cleavage reactor (R), there would be the risk of undesired concentration of MSBE in the circuit in the case of recycling without discharge of the sidestream, and this can be avoided very easily by the discharge in the sidestream. The sidestream 11 can be utilized thermally, used as a feedstock for a synthesis gas plant or used as a fuel component.

Column (K6), FIGS. 1 & 2

In column (K6), according to the invention, medium boilers formed in the reaction part, for example dimethoxymethane and/or isoprene, are removed from the return stream 10 consisting predominantly of MTBE and methanol.

Preferably, the material separation is carried out in a distillation column which has 20 to 75 theoretical plates, preferably 25 to 55 and more preferably 30 to 45 theoretical plates. The column, depending on the number of plates realized, the composition of the recycle stream and the amount of the medium boilers formed in the cleavage reactor (R), for example dimethoxymethane and/or isoprene, is preferably operated with a reflux ratio in the range from 10 to 150, especially in the range from 30 to 100. The column is preferably operated with an operating pressure of 0.05 to 1 MPa$_{(abs)}$, preferably of 0.3 to 0.6 MPa$_{(abs)}$. To heat the column, for example, steam can be used. According to the operating pressure selected, the condensation can be effected against cooling brine, cooling water or air. The top vapours of the column can be condensed completely or only partially, such that the top product 14 can be drawn off either in liquid or vapourous form. The top product 14 can be utilized thermally or used as a feedstock of a synthesis gas plant.

When columns are used in the process according to the invention, for example the columns designated K1, K2, K3, K4, K5 and K6 in FIGS. 1 to 4, they can be provided with internals, which, for example, are composed of trays, rotating internals, random packings and/or structured packings.

In the case of column trays, for example, the following types can be used:

Trays with bores or slots in the tray plate.
Trays with necks or chimneys which are covered by caps or hoods.
Trays with bores in the tray plate, which are covered by movable valves.
Trays with special constructions.

In columns with rotating internals, the reflux can be sprayed, for example, by means of rotating funnels, or spread as a film on a heated tube wall with the aid of a rotor.

In the case of use of columns with random packings comprising various packing materials, the packing materials may consist of almost all materials, especially of steel, stainless steel, copper, carbon, stoneware, porcelain, glass or plastics, and have a wide variety of different shapes, especially the shape of spheres, rings with smooth or profiled surfaces, rings with internal struts or wall breaches, wire mesh rings, saddles and spirals.

Structured packings with regular/ordered geometry may consist, for example, of sheet metal or fabric. Examples of such packings are Sulzer BX fabric packings made of metal or plastic, Sulzer Mellapak lamellar packings made of sheet metal, high-performance packings from Sulzer such as Mella-pakPlus, and structured packings from Sulzer (Optiflow), Montz (BSH) and Kühni (Rombopak).

Isobutene Workup

The isobutene-rich stream 7 obtained in step b) of the process can be worked up to isobutene with higher purities. This removes methanol, dimethyl ether (DME) and water in particular. By way of example, a workup of stream 7 from the preferred embodiments shown in FIGS. 1 to 4 is therefore described. The methanol in stream 7 can be removed by processes known per se, for example by extraction. The extraction of methanol from stream 7 can be carried out, for example, with water or an aqueous solution as an extractant, for example in an extraction column. Preference is given to performing the extraction with water or an aqueous solution in an extraction column, which preferably has 4 to 16 theoretical plates. The extractant flows through the extraction column preferably in countercurrent in relation to the stream to be extracted. The extraction is preferably carried out at a temperature of 15 to 50° C., preferably 25 to 40° C. For example, in the case of use of an extraction column with more than 6 theoretical plates which is operated at a pressure of 0.9 MPa$_{(abs)}$ and a temperature of 40° C., a water-saturated isobutene with a residual content of methanol of less than 500 ppm by mass, preferably less than 100 ppm by mass and more preferably less than 30 ppm by mass of methanol can be obtained.

The methanol-containing water extract obtained in the extraction can be separated by distillation into water and methanol. The water can be recycled into the extraction stage as the extractant. The methanol can be utilized for customary industrial syntheses, for example esterifications or etherifications.

The moist isobutene stream from the extraction column can be worked up to dry isobutene in one or more further distillation columns by removing water and optionally DME. The dry isobutene is obtained as the bottom product. In the condensation system at the top of the column, after a phase separation, water can be drawn off in liquid form, and DME with residual amounts of isobutene in liquid and/or gaseous form. A distillation column used with preference for the drying has preferably 30 to 80 theoretical plates, preferably 40 to 65 theoretical plates. The reflux ratio is, depending on the number of plates realized and the required purity of the isobutene, preferably less than 60, preferentially less than 40. The operating pressure of column K2 can preferably be set in the range from 0.1 to 2.0 MPa$_{(abs)}$. The DME-rich stream obtained at the top of the column can, if necessary, be separated further by distillation.

A portion of the DME can optionally be removed from stream 7 as early as in the course of distillation (K3), by operating the condenser on the distillation column or reactive distillation column as a partial condenser. Therein, the C$_4$ fraction present in the top product can be condensed and a portion of the gaseous dimethyl ether can be drawn off as an offgas stream.

A workup of isobutene by extraction and distillation is described in detail, for example, in DE 102 38 370. Preferably, methanol is removed from the top stream 7 comprising isobutene by extraction, and DME and if appropriate water are removed by distillation from the isobutene extracted.

More preferably, in the process according to the invention, a column for removing DME and water is used which has a decanter for removing water, which is present in the sidestream of the column. The incorporation of the decanter in the sidestream of the column allows isobutene losses to be minimized. Such a process is also described, for example, in application DE 102 38 370. In this case, the moist isobutene stream from the extraction is, if appropriate after removal of residual heterogeneous water, for example by means of a decanter or coalescer, fed into a column. DME is obtained at the top of the column and dry isobutene in the bottoms. Below or above the reactant introduction site, a sidestream from the column is withdrawn in liquid form and conducted into a decanter. In the decanter, the aqueous phase is separated from the water-depleted organic phase. The water is discharged; the organic phase is recycled into the column. The removal of the stream to the side decanter is preferably effected below the column feed, the recycling of the stream from the decanter into the column below the withdrawal point.

The column preferably has a number of plates of 30 to 80 theoretical plates, preferably of 40 to 65 theoretical plates. The isobutene to be purified is preferably fed in above plate 15 to 30, in each case counted from the top. Preferably, two to five plates above the feed point, the entire condensate of this plate is drawn off and passed into the decanter. After the water has been removed, the organic phase is recycled into the column one or two plates lower. The reflux ratio of the column is, depending on the number of plates realized and the required purity of the isobutene, preferably less than 60, preferentially less than 40. The operating pressure of the column is preferably in the range from 0.1 to 2.0 MPa$_{(abs)}$, more preferably in the range from 1.0 to 1.5 MPa$_{(abs)}$.

The isobutene obtained in this way may have, for example, the composition listed in table 5:

TABLE 5

Typical composition of isobutene available on the market
Proportions by mass [kg/kg]

| | |
|---|---|
| C$_3$ hydrocarbons | <0.000100 |
| butanes | <0.001000 |
| isobutene | >0.999000 |
| 1-butene/2-butenes | <0.001000 |
| methanol | <0.000030 |
| C$_5$ hydrocarbons | <0.000500 |
| water | <0.000050 |
| oxygenates | <0.000010 |

Oxygenates: For example DME, dimethoxymethane

The linear butenes (1-butene, 2-butenes) present in the isobutene cannot be removed therefrom in an industrially viable manner. The linear butenes are formed, inter alia, from the cleavage of MSBE, which may be present in the MTBE.

Therefore, complete removal of MSBE in the column (K2) allows the formation of the linear butenes to be prevented. In order to limit the distillation costs, it may, however, be advantageous to permit a low concentration of MSBE. This is possible especially when, in step a) of the process, a catalyst which decomposes MTBE more rapidly than MSBE is used.

According to the purity requirements, however, if required, smaller concentrations of the secondary components are also achievable.

The isobutene prepared by the process according to the invention can, for example, be used to prepare methacrylic acid, methyl methacrylate, diisobutene, polyisobutene, alkylphenols, methallyl chloride or methallyl sulfonates. In particular, it may be advantageous to use both the methanol obtained in the cleavage and the isobutene to prepare methyl methacrylate. Such a process of preparing methyl methacrylate is described, for example, in EP 1 254 887, to which explicit reference is made.

The examples which follow are intended to illustrate the invention.

EXAMPLES

Example 1

A cleavage was carried out in a tubular reactor with a heating jacket, through which a heat carrier oil (Marlotherm SH from Sasol Olefins & Surfactants GmbH) flowed. The catalyst used was magnesium-doped silica-alumina. The catalyst was prepared according to patent application DE 10 2006 040432, see example 2. The reactant used was high-purity MTBE, which is normally not used as a fuel additive but as a solvent (DRIVERON-S from Evonik Oxeno GmbH).

Before entry into the reactor, the MTBE was evaporated completely in an evaporator at 300° C. The cleavage was carried out at a temperature of 280° C. (temperature of the Marlotherm in the feed of the reactor jacket); the pressure was kept at a constant 0.7 $MPa_{(abs)}$ by a pressure-maintaining means at the end of the reactor. The MTBE feed was regulated to a constant 1500 g/h, which corresponds to a WHSV of 4.78 $h^{-1}$ at an amount of catalyst of 314 g. The gaseous cleavage mixture leaving the reactor was condensed fully and analyzed by gas chromatography.

After a service life of 1006 hours, the conversion of the MTBE under the selected reaction conditions was 98%. In addition to the isobutene and methanol cleavage products, the by-products listed in table 6 were detected.

TABLE 6

Analyses of reactor feed and reactor effluent (in each case proportions by mass)

| Reactor feed | | Reactor effluent | |
|---|---|---|---|
| Component | Proportion | Trace components | Proportion |
| MTBE | 99.949% | DME | 0.955% |
| 2-methoxybutane | < dl | $C_8$ hydrocarbons | 0.063% |
| isoprene | < dl | isobutane | 0.010% |
| $C_5$ hydrocarbons | 0.026% | isoprene | 0.003% |
| methanol | 0.013% | dimethoxymethane | 0.010% |
| 3-methoxy-1-butene | 0.004% | 1,3-butadiene | 0.0006% |
| remainder | 0.008% | n-butenes | <0.0005% | dl: detection limit

It is found that further by-products (isoprene, dimethoxymethane, isobutane) are additionally formed in a relatively low concentration as well as dimethyl ether (DME) and $C_8$ hydrocarbons. The formation of 1,3-butadiene is attributed to the presence of 3-methoxy-1-butene in the MTBE used. Since the raw material is virtually free of 2-methoxybutane (MSBE), no significant amounts of linear butenes are formed.

Explanations for Examples 2 and 3

In examples 2 and 3 which follow, calculations were carried out with the steady-state simulation program ASPEN Plus (version 12.1 from AspenTech), which represent the effects of the medium boiler formation in the overall process.

In order to obtain transparent, reproducible data, only generally available material data were used. In addition, the use of a reactive distillation was dispensed with in all variants. These simplifications make it possible for the person skilled in the art to easily appreciate the calculations. Although the methods used do not have sufficient accuracy for the design of industrial plants, the qualitative differences in the circuits are correctly detected. In all variants detailed, the MTBE conversion can be increased by using a reactive distillation.

In the examples, the "UNIFAC-DMD" property method (see J. Gmehling, J. Li, and M. Schiller, Ind. Eng. Chem. Res. 32, (1993), pp. 178-193) was used. For the reactor R, a reactor volume of 100 l was modelled in each case, assuming a filling with a catalyst which consists in a formal sense of magnesium oxide, aluminium oxide and silicon oxide, and whose preparation is described in DE 10 2006 040432.

For the reactor modelling, a kinetic reactor model was used in the calculations, which is based on extensive experimental test data with this catalyst. The examples therefore in each case also specify the reaction temperatures which were assumed in the reactor modelling. Since the composition of the input and output streams of the reaction stage are also specified in each case, it is possible for the person skilled in the art to follow the calculations of the example without knowing the exact equations for the kinetics by simulating the reactors with fixed conversions.

Example 2

Example 2 corresponds to the variant represented in FIG. 3. As the feed to the MTBE cleavage plant, according to FIG. 3, an MTBE stream 1a (starting MTBE) of 100 kg/h with the composition listed in table 7 is assumed (typical fuel MTBE, compare with table 2).

TABLE 7

Composition of the MTBE input stream 1a assumed into the MTBE cleavage plant for example 2.

| | Starting MTBE 1a |
|---|---|
| Mass flow [kg/h] | 100.0 |
| Proportions by mass [kg/kg] | |
| dimethyl ether (DME) | |
| isobutene | |
| isobutane | |
| 1-butene/2-butenes | 0.001000 |
| $C_5$ hydrocarbons | 0.001500 |
| isoprene | |
| dimethoxymethane | |
| MTBE | 0.979650 |
| 2-methoxybutane (MSBE) | 0.003000 |

TABLE 7-continued

Composition of the MTBE input stream 1a assumed into the MTBE cleavage plant for example 2.

|  | Starting MTBE 1a |
|---|---|
| methanol | 0.008500 |
| tert-butanol (TBA) | 0.003000 |
| water | 0.000050 |
| diisobutene | 0.003300 |

The starting MTBE 1a is mixed with the recycle stream 10 and fed into the column K1. The recycle stream 10 is the distillate stream of the column K4, which contains the complete amount of the MTBE unconverted in the cleavage reactor (R), and the secondary diisobutene, MSBE and methanol components. In addition, this stream also contains medium boilers formed in the cleavage reactor, in this example isoprene and dimethoxymethane. The assumed composition of the recycle stream 10 and of the feed stream to column K1 which arises from the mixing is shown in table 8.

TABLE 8

Composition of the recycle stream 10 and of the feed stream of column K1 for example 2.

|  | Recycle stream 10 | Feed K1 |
|---|---|---|
| Mass flow [kg/h] | 10.2 | 110.2 |
| Proportions by mass [kg/kg] |  |  |
| DME | 0.000256 | 0.000024 |
| isobutene | 0.002094 | 0.000193 |
| isobutane |  |  |
| 1-butene/2-butenes | 0.000013 | 0.000909 |
| $C_5$ hydrocarbons |  | 0.001362 |
| isoprene | 0.002183 | 0.000201 |
| dimethoxymethane | 0.000384 | 0.000035 |
| MTBE | 0.593166 | 0.944003 |
| MSBE | 0.017945 | 0.004378 |
| methanol | 0.376157 | 0.042411 |
| tert-butanol | 0.000030 | 0.002726 |
| water | 0.000016 | 0.000047 |
| diisobutene | 0.007758 | 0.003711 |

The task of column K1 in example 2 is, in addition to the removal of the $C_4$ and $C_5$ hydrocarbons present in the starting MTBE, in particular the discharge of the medium boilers which are present in the recycle stream and have formed in the cleavage reactor (R), in this example isoprene and dimethoxymethane. The column has 55 theoretical plates and is operated at a reflux ratio of 116 and at a pressure of 0.3 $MPa_{(abs)}$. The material is added above plate 22, counted from the top. The top temperature is 72.4° C.; the bottom temperature is 87.3° C. The distillate of this column 2 has a residual content of approx. 68% by mass of MTBE. Increasing the reflux ratio and/or the number of plates would allow the MTBE content to be reduced. The bottom product is free of low boilers present in the MTBE and in the recycle stream ($C_4$ and $C_5$ hydrocarbons). Likewise removed are the medium boilers isoprene and dimethoxymethane.

TABLE 9

Composition of distillate stream 2 and of bottom product 3 of column K1 for example 2.

|  | Distillate K1 2 | Bottom product K1 3 |
|---|---|---|
| Mass flow [kg/h] | 2.4 | 107.8 |
| Proportions by mass [kg/kg] |  |  |
| DME | 0.001097 |  |
| isobutene | 0.008980 |  |
| isobutane |  |  |
| 1-butene/2-butenes | 0.042263 |  |
| $C_5$ hydrocarbons | 0.063312 |  |
| isoprene | 0.009361 |  |
| dimethoxymethane | 0.000822 | 0.000018 |
| MTBE | 0.682321 | 0.949754 |
| MSBE | 0.000073 | 0.004473 |
| methanol | 0.189593 | 0.039176 |
| tert-butanol |  | 0.002786 |
| water | 0.002179 |  |
| diisobutene |  | 0.003793 |

The bottom product of column K1 which has been freed of low and medium boilers is fed into column K2. The separating task of column K2 is the removal of diisobutene and MSBE. The column has 95 theoretical plates and is operated at a reflux ratio of 4.2 and at a pressure of 0.95 $MPa_{(abs)}$. The material is added above plate 32 counted from the top. The top temperature is 140.5° C.; the bottom temperature is 154.4° C. The top product 5 is a gaseous fraction which is free of diisobutene and contains only 2100 ppm by mass of MSBE; see table 10. The content of MTBE is approx. 95.5% by mass. The content of MTBE in the bottom product 4 is approx. 61.8% by mass. Increasing the reflux ratio and/or the separating performance would allow the content of MTBE in the bottom product to be reduced further.

TABLE 10

Composition of the distillate stream 5 and bottom stream 4 of column K1 for example 2.

|  | Distillate K2 5 | Bottom product K2 4 |
|---|---|---|
| Mass flow [kg/h] | 106.0 | 1.8 |
| Proportions by mass [kg/kg] |  |  |
| DME |  |  |
| isobutene |  |  |
| isobutane |  |  |
| 1-butene/2-butenes |  |  |
| $C_5$ hydrocarbons |  |  |
| isoprene |  |  |
| dimethoxymethane | 0.000018 |  |
| MTBE | 0.955228 | 0.618100 |
| MSBE | 0.002100 | 0.148272 |
| methanol | 0.039822 |  |
| tert-butanol | 0.002832 | 0.000012 |
| water |  |  |
| diisobutene |  | 0.233617 |

The distillate stream 5 of column K2 is, after further heating to reaction temperature, fed to the cleavage reactor (R). The reactor is operated at 305° C. and 0.85 $MPa_{(abs)}$. Under these reaction conditions, an MTBE conversion of approx. 94% is obtained; the conversion of MSBE is approx. 18%. At these high reaction temperatures, the medium boilers isoprene and dimethoxymethane are formed in side reactions. Under the reaction conditions, the reactor effluent contains approx. 70 ppm of dimethoxymethane and approx. 210 ppm of isoprene. Isobutane is present to an extent of approx. 220 ppm. The composition of the reactor effluent 6 is shown by table 11.

TABLE 11

Composition of the reactor effluent 6 and of the distillate stream 7 and of the bottom stream 8 of column K3 for example 2.

|  | Reactor effluent 6 | Distillate K3 7 | Bottom product K3 8 |
|---|---|---|---|
| Mass flow [kg/h] | 106.0 | 63.5 | 42.6 |
| Proportions by mass [kg/kg] |  |  |  |
| DME | 0.004873 | 0.008098 | 0.000061 |
| isobutene | 0.572525 | 0.955934 | 0.000500 |
| isobutane | 0.000219 | 0.000366 |  |
| 1-butene/2-butenes | 0.000242 | 0.000402 | 0.000003 |
| C$_5$ hydrocarbons |  |  |  |
| isoprene | 0.000210 |  | 0.000521 |
| dimethoxymethane | 0.000071 |  | 0.000176 |
| MTBE | 0.056836 |  | 0.141632 |
| MSBE | 0.001720 |  | 0.004286 |
| methanol | 0.359580 | 0.034866 | 0.844037 |
| tert-butanol | 0.000422 |  | 0.001051 |
| water | 0.002559 | 0.000333 | 0.005880 |
| diisobutene | 0.000743 |  | 0.001852 |

The reactor effluent 6 is partially condensed and fed in biphasic form to column K3. The column has 42 theoretical plates and is operated at a reflux ratio of 0.7 and at a pressure of 0.65 MPa$_{(abs)}$. The material is added above plate 28, counted from the top. The top temperature is 51.3° C.; the bottom temperature is 117.1° C. The top product 7 is isobutene with a purity of greater than 95% by mass of isobutene; see table 11. Isoprene is removed completely via the bottom, as is likewise dimethoxymethane. The limits required in a typical isobutene specification for linear butenes (<1000 ppm by mass) and C$_5$ hydrocarbons (<1000 ppm by mass) are complied with reliably. An extraction with water can, if required, remove the methanol, the residual water and DME can be removed by a subsequent distillation and the isobutene can be concentrated to a purity greater than 99.9% by mass.

The bottom product 8 of column K3 consists predominantly of unconverted MTBE (approx. 14% by mass) and methanol (approx. 84% by mass). In addition, this stream contains the complete amount of the medium boilers isoprene and dimethoxymethane formed by reaction. In addition, among other substances, unconverted MSBE, TBA, water, and diisobutene formed by reaction are present. This stream is fed to column K4.

TABLE 12

Composition of the bottom stream 9 of column K4 for example 2.

|  | Bottom product K4 9 |
|---|---|
| Mass flow [kg/h] | 32.4 |
| Proportions by mass [kg/kg] |  |
| DME |  |
| isobutene |  |
| isobutane |  |
| 1-butene/2-butenes |  |
| C$_5$ hydrocarbons |  |
| isoprene |  |
| dimethoxymethane | 0.000111 |
| MTBE |  |
| MSBE |  |
| methanol | 0.990796 |
| tert-butanol | 0.001372 |
| water | 0.007719 |
| diisobutene |  |

Column K4 has 35 theoretical plates and is operated at a reflux ratio of 1.9 and at a pressure of 0.1 MPa$_{(abs)}$. The material is added above plate 10, counted from the top. The top temperature is 51.3° C.; the bottom temperature is 64.4° C. The composition of the bottom product 9 is shown by table 12; the composition of the distillate 10 of column K4 is also listed in table 8. In the column, MTBE, MSBE and diisobutene are distilled via the top with a certain amount of methanol. This exploits the azeotrope formation of these components with methanol. In addition, all low boilers and medium boilers (DME, butenes, C$_5$ hydrocarbons, isoprene, dimethoxymethane) are also removed very substantially, such that a very pure bottom product with more than 99% by mass of methanol can be obtained. The distillate 10 of column K4 is added to the feed of column K1.

Example 3

Example 3 corresponds to the variant shown in FIG. 4. As the feed to the MTBE cleavage unit, according to FIG. 4, an MTBE stream 1a (starting MTBE) of 100 kg/h with the composition listed in table 13 is assumed.

Compared to example 2 (see table 7), this starting stream has a lower content of MSBE and diisobutene, and so a removal of these components upstream of the reaction part can be dispensed with, and the discharge can be effected according to FIG. 4 in the sidestream of column K5.

TABLE 13

Composition of the MTBE input stream 1a into the MTBE cleavage plant for example 3.

|  | Starting MTBE 1a |
|---|---|
| Mass flow [kg/h] | 100.0 |
| Proportions by mass [kg/kg] |  |
| DME |  |
| isobutene |  |
| isobutane |  |
| 1-butene/2-butenes | 0.001000 |
| C$_5$ hydrocarbons | 0.001500 |
| isoprene |  |
| dimethoxymethane |  |
| MTBE | 0.981450 |
| MSBE | 0.002000 |
| methanol | 0.008500 |
| tert-butanol | 0.003000 |
| water | 0.000050 |
| diisobutene | 0.002500 |

The starting MTBE 1a is mixed with the recycle stream 12 and fed into column K1.

The recycle stream 12 is the distillate stream of column K5, which contains the majority of the MTBE unconverted in the reaction part (R), the secondary diisobutene and MSBE components, and methanol. In addition, this stream also contains medium boilers formed in the reaction part, in this example isoprene and dimethoxymethane. The composition of the return stream 12 and of the feed stream to column K1 which arises from the mixing is shown in table 14.

TABLE 14

Composition of the recycle stream 12 and of the feed stream of column K1 for example 3.

|  | Recycle stream 12 | Feed K1 |
|---|---|---|
| Mass flow [kg/h] | 6.2 | 106.2 |
| Proportions by mass [kg/kg] | | |
| DME | 0.000291 | 0.000017 |
| isobutene | 0.003306 | 0.000193 |
| isobutane | | |
| 1-butene/2-butenes | 0.000021 | 0.000943 |
| $C_5$ hydrocarbons | 0.000085 | 0.001417 |
| isoprene | 0.003550 | 0.000207 |
| dimethoxymethane | 0.000620 | 0.000036 |
| MTBE | 0.824913 | 0.972322 |
| MSBE | 0.005645 | 0.002213 |
| methanol | 0.161560 | 0.017425 |
| tert-butanol | | 0.002825 |
| water | 0.000009 | 0.000048 |
| diisobutene | | 0.002354 |

The task of column K1 is, in addition to the removal of the $C_4$ and $C_5$ hydrocarbons present in the starting MTBE, in particular the discharge of the medium boilers which are present in the recycle stream and have formed in the reaction part, in this example isoprene and dimethoxymethane. The column has 60 theoretical plates and is operated at a reflux ratio of 197 and at a pressure of 0.3 $MPa_{(abs)}$. The material is added above plate 25, counted from the top. The top temperature is 48.2° C.; the bottom temperature is 105.8° C. The distillate 2 of this column has a residual content of 15% by mass of MTBE. Increasing the reflux ratio and/or the number of plates would allow the MTBE content to be reduced further. The bottom product is free of low boilers ($C_4$ and $C_5$ hydrocarbons) present in the MTBE and in the recycle stream. Likewise removed completely are the medium boilers isoprene and dimethoxymethane.

TABLE 15

Composition of distillate stream 2 and of bottom product 3 of column K1 for example 3.

|  | Distillate K1 2 | Bottom product K1 3 |
|---|---|---|
| Mass flow [kg/h] | 0.4 | 105.8 |
| Proportions by mass [kg/kg] | | |
| DME | 0.004469 | |
| isobutene | 0.050785 | |
| isobutane | | |
| 1-butene/2-butenes | 0.248372 | |
| $C_5$ hydrocarbons | 0.372063 | |
| isoprene | 0.054157 | |
| dimethoxymethane | 0.008717 | |
| MTBE | 0.150000 | 0.975456 |
| MSBE | 0.000017 | 0.002221 |
| methanol | 0.111419 | 0.017067 |
| tert-butanol | | 0.002836 |
| water | | 0.000048 |
| diisobutene | | 0.002363 |

The bottom product of column K1, which has been freed of low and medium boilers, is compressed to reaction pressure in liquid form, heated and evaporated, and fed in gaseous form, with a temperature which corresponds to the reaction temperature in the reactor, to the reactor part (R). Reaction temperature, reactor pressure, conversions and by-product spectrum remain unchanged compared to example 2. The reactor effluent thus contains approx. 60 ppm of dimethoxymethane and approx. 210 ppm of isoprene. Isobutane is present to an extent of approx. 220 ppm. The composition of the reactor effluent 6 is shown by table 16.

TABLE 16

Composition of the reactor effluent 6 and of the distillate stream 7 and of the bottom stream 8 of column K3 for example 3.

|  | Reactor effluent 6 | Distillate K3 7 | Bottom product K3 8 |
|---|---|---|---|
| Mass flow [kg/h] | 105.8 | 64.7 | 41.1 |
| Proportions by mass [kg/kg] | | | |
| DME | 0.004662 | 0.007599 | 0.000044 |
| isobutene | 0.584796 | 0.956378 | 0.000500 |
| isobutane | 0.000219 | 0.000359 | |
| 1-butene/2-butenes | 0.000256 | 0.000417 | 0.000003 |
| $C_5$ hydrocarbons | 0.000005 | | 0.000013 |
| isoprene | 0.000212 | | 0.000543 |
| dimethoxymethane | 0.000056 | | 0.000143 |
| MTBE | 0.058040 | | 0.149304 |
| MSBE | 0.001819 | | 0.004680 |
| methanol | 0.344041 | 0.034895 | 0.830158 |
| tert-butanol | 0.000423 | | 0.001087 |
| water | 0.002525 | 0.000351 | 0.005944 |
| diisobutene | 0.002947 | | 0.007581 |

The reactor effluent 6 is partially condensed and fed to the column K3 in biphasic form. The number of plates, material addition point, reflux ratio and operating pressure of column K3 remain unchanged compared to example 2. The top temperature is 51.3° C.; the bottom temperature is 116.9° C. The top product 7 is isobutene with a purity of greater than 95% by mass of isobutene; see table 16. Isoprene is removed completely via the top, as is likewise dimethoxymethane. The limits required in a typical isobutene specification for linear butene (<1000 ppm by mass) and $C_5$ hydrocarbons (<1000 ppm by mass) are complied with reliably. An extraction with water allows the methanol to be removed if required; the residual water and DME can be removed by a subsequent distillation, and the isobutene can be concentrated to a purity greater than 99.9% by mass.

The bottom part 8 of column K3 consists predominantly of unconverted MTBE (approx. 15% by mass) and methanol (approx. 84% by mass). In addition, this stream contains the complete amount of the medium boilers isoprene and dimethoxymethane formed by the reaction. In addition, among other substances, unconverted MSBE, TBA, water, and diisobutene formed by reaction are present. This stream is fed to column K5.

TABLE 17

Composition of the bottom stream 9 and of the sidestream 11 of column K5 for example 3.

|  | Bottom product K5 9 | Sidestream K5 11 |
|---|---|---|
| Mass flow [kg/h] | 30.4 | 4.5 |
| Proportions by mass [kg/kg] | | |
| DME | | |
| isobutene | | |
| isobutane | | |
| 1-butene/2-butenes | | |
| C$_5$ hydrocarbons | | |
| isoprene | | 0.000076 |
| dimethoxymethane | | 0.000186 |
| MTBE | | 0.229335 |
| MSBE | | 0.034997 |
| methanol | 0.990493 | 0.666034 |
| tert-butanol | 0.001457 | 0.000077 |
| water | 0.008030 | 0.000008 |
| diisobutene | | 0.069283 |

Column K5 has 62 theoretical plates and is operated at a reflux ratio of 14.5 and at a pressure of 0.15 MPa$_{(abs)}$. The material is added above plate 36, counted from the top. The sidestream is withdrawn in liquid form at plate 25, counted from the top. The top temperature is 61.0° C.; the bottom temperature is 75.1° C. The composition of the bottom product 9 and of the sidestream 11 are shown in table 17; the composition of the distillate 10 of column K4 is also listed in table 14.

In the column, the predominant portion of the MTBE and MSBE present in the feed stream 8 is distilled via the top with a small amount of methanol. This exploits the azeotrope formation of these components with methanol. In addition, all low boilers (DME, butenes and pentanes) and the medium boilers formed in the reaction part (isoprene, dimethoxymethane) are also removed via the top. The distillate 12 is recycled into the reaction part.

The sidestream 11 contains all of the diisobutene, and additionally MTBE, methanol and MSBE, and the medium boilers isoprene and dimethoxymethane in traces. As a result of the discharge of MSBE, this component cannot accumulate to undesired concentrations in the circuit. Limiting the concentration of MSBE in the circuit thus simultaneously prevents an impermissibly high level of linear butenes formed by cleavage of MSBE in the reaction part in the isobutene product.

The bottom product 9 obtained is very pure methanol which has a purity of more than 99% by mass and is free of diisobutene. The sole secondary components present are TBA and water. If required, the methanol can be freed of TBA and water in a further distillation step and thus concentrated to even higher purities.

The invention claimed is:

1. A process for preparing isobutene from a MTBE-comprising mixture, the process comprising:
    A) in a reactor R, cleaving a mixture obtained from an MTBE-comprising feedstock and/or a first MTBE-comprising stream, affording a first product stream of reaction products comprising isobutene, isoprene, methanol, dimethoxymethane, MTBE, and by-products, the by-products consisting of
        a1) high boilers having a boiling range above 55° C. at a pressure of 0.1 MPa;
        a2) medium boilers having a boiling range of 12 to 55° C. at a pressure of 0.1 MPa; and
        a3) low boilers having a boiling range below 12° C. at a pressure of 0.1 MPa;
    B) distillatively separating the first product stream into a second product stream which comprises the isobutene and low boilers, and a third product stream which comprises MTBE, methanol, medium boilers, and high boilers;
    C) distillatively separating the third product stream to obtain a second MTBE-comprising stream and a first methanol-comprising high boiler stream;
    D) recycling the second MTBE-comprising stream into the cleaving A), the medium boilers being removed completely or partially before the recycling D) from the second MTBE-comprising stream;
    wherein at least one of dimethoxymethane and isoprene are removed from a the second MTBE comprising stream recycled to the cleaving.

2. The process according to claim 1, wherein the cleaving A) is effected over a solid catalyst.

3. The process according to claim 1, wherein the cleaving A) of the mixture is carried out within a temperature range from 150 to 500° C.

4. The process according claim 1, wherein the cleaving A) of the mixture is carried out within a pressure range from 0.05 to 2 MPa.

5. The process according to claim 1, wherein the cleaving A) is effected at an entrance temperature into the reactor of at least 150° C.

6. The process according to claim 1, wherein the stream of MTBE-comprising feedstock is fed to the cleaving A) and is subjected beforehand to a distillation at an operating pressure of least 0.05 MPa above an operating pressure of the cleaving A).

7. The process according to claim 1, wherein the distillatively separating of the first product stream which is connected downstream of the cleaving A), is carried out at an operating pressure of at least 0.05 MPa below an operating pressure of the cleaving A).

8. The process according to claim 1, comprising:
    combining the second MTBE-comprising stream with the MTBE-comprising feedstock, to form an overall stream, and high boilers, medium boilers, and/or low boilers are removed from the overall stream.

9. The process according to claim 1, wherein the distillatively separating C) of the third product stream is effected in at least two distillation columns to remove the low boilers, medium boilers and high boilers.

10. The process according to claim 9, wherein the low boilers and medium boilers are removed as a top product in the first distillation column, and the high boilers as a bottom product in a further distillation column.

11. The process according to claim 1, wherein the low boilers comprise dimethyl ether and/or at least one C$_4$ hydrocarbon.

12. The process according to claim 1, wherein the medium boilers comprise dimethoxymethane and/or at least one C$_5$ hydrocarbon.

13. The process according to claim 1, wherein the medium boilers comprise isoprene.

14. The process according to claim 1, wherein the high boilers comprise at least one selected from the group consisting of 2-methoxybutane and a C$_8$ hydrocarbon.

15. The process according to claim 2, wherein the cleaving A) of the mixture is carried out within a temperature range from 150 to 500° C.

16. The process according claim 2, wherein the cleaving A) of the mixture is carried out within a pressure range from 0.05 to 2 MPa.

17. The process according claim 3, wherein the cleaving A) of the mixture is carried out within a pressure range from 0.05 to 2 MPa.

18. The process according claim 15, wherein the cleaving A) of the mixture is carried out within a pressure range from 0.05 to 2 MPa.

19. The process according to claim 1, further comprising:
    removing dimethoxymethane and isoprene from the second MTBE-comprising stream after the distillative separation (C) and before the recycling (D).

20. The process according to claim 1, further comprising:
    removing at least a portion of at least one of dimethoxymethane and isoprene from the second MTBE-comprising stream after the distillative separation (C) and before the recycling (D).

* * * * *